(12) United States Patent
Choi et al.

(10) Patent No.: US 9,354,309 B2
(45) Date of Patent: May 31, 2016

(54) APPARATUS AND METHOD FOR REALIZING SYNCHRONIZATION IMAGE

(71) Applicant: SAMSUNG MEDISON CO., LTD., Gangwon-do (KR)

(72) Inventors: Seok-won Choi, Gangwon-do (KR); Dong-gyu Hyoun, Gangwon-do (KR); Dong-hyun Lee, Gangwon-do (KR)

(73) Assignee: SAMSUNG MEDISON CO., LTD., Hongcheon-Gun, Gangwon-Do (KR)

( * ) Notice: Subject to any disclaimer, the term of this patent is extended or adjusted under 35 U.S.C. 154(b) by 161 days.

(21) Appl. No.: 13/734,535

(22) Filed: Jan. 4, 2013

(65) Prior Publication Data

US 2013/0176824 A1 Jul. 11, 2013

(30) Foreign Application Priority Data

Jan. 6, 2012 (KR) .................. 10-2012-0002033

(51) Int. Cl.
*A61B 8/08* (2006.01)
*A61B 8/00* (2006.01)
*G01S 15/62* (2006.01)
*G01S 15/89* (2006.01)
(Continued)

(52) U.S. Cl.
CPC . *G01S 15/62* (2013.01); *A61B 8/08* (2013.01); *A61B 8/488* (2013.01); *A61B 8/5223* (2013.01); *G01S 7/52071* (2013.01); *G01S 15/8984* (2013.01); *G01S 15/8993* (2013.01); *A61B 8/0883* (2013.01); *A61B 8/4483* (2013.01); *A61B 8/466* (2013.01); *A61B 8/483* (2013.01); *G01S 15/8977* (2013.01); *G06T 7/2006* (2013.01); *G06T 2207/10132* (2013.01)

(58) Field of Classification Search
CPC .............. A61B 8/12; A61B 8/00; A61B 8/14; G06K 9/00
USPC ................. 600/441, 443, 440, 453, 454, 437; 382/133; 367/93; 324/307
See application file for complete search history.

(56) References Cited

U.S. PATENT DOCUMENTS 5,622,174 A * 4/1997 Yamazaki ...................... 600/441
6,159,151 A * 12/2000 Bonnefous ..................... 600/440
(Continued)

FOREIGN PATENT DOCUMENTS

EP 0228069 A2 7/1987
JP 2006-000421 A 1/2006
(Continued)

OTHER PUBLICATIONS

Korean Notice of Allowance, w/ English translation thereof, issued in Korean Patent Application No. KR 10-2012-0002033 dated Oct. 10, 2013.
(Continued)

*Primary Examiner* — Mohamed Barakat
(74) *Attorney, Agent, or Firm* — McDermott Will & Emery LLP

(57) ABSTRACT

A method and apparatus for realizing a synchronization image. The method includes transmitting an ultrasonic signal to an object, obtaining vector components of at least two points included in the object based on an echo signal reflected from the object, and realizing a synchronization image of the object, which indicates whether motions of the at least two points have been synchronized, by using the obtained vector component.

19 Claims, 6 Drawing Sheets

(51) Int. Cl.
*G01S 7/52* (2006.01)
*G06T 7/20* (2006.01)

(56) References Cited

U.S. PATENT DOCUMENTS

| | | | |
|---|---|---|---|
| 7,175,598 B2 * | 2/2007 | Yoneyama | 600/443 |
| 7,439,736 B2 * | 10/2008 | Meaney et al. | 324/307 |
| 2005/0096543 A1 * | 5/2005 | Jackson et al. | 600/441 |
| 2008/0081998 A1 | 4/2008 | Pan et al. | |
| 2008/0300487 A1 | 12/2008 | Govari et al. | |
| 2009/0270732 A1 * | 10/2009 | Abe et al. | 600/443 |
| 2010/0174193 A1 | 7/2010 | Lee et al. | |
| 2010/0280385 A1 * | 11/2010 | Palti | 600/454 |
| 2012/0014588 A1 * | 1/2012 | Chono | 382/133 |

FOREIGN PATENT DOCUMENTS

| | | |
|---|---|---|
| JP | 2009-005829 A | 1/2009 |
| KR | 10-2008-0106860 A | 12/2008 |
| KR | 10-2010-0129569 A | 12/2010 |
| WO | 0245587 A1 | 6/2002 |

OTHER PUBLICATIONS

Extended European Search Report issued in European Application No. 13150129.8 dated Apr. 10, 2013.

* cited by examiner

FIG. 6
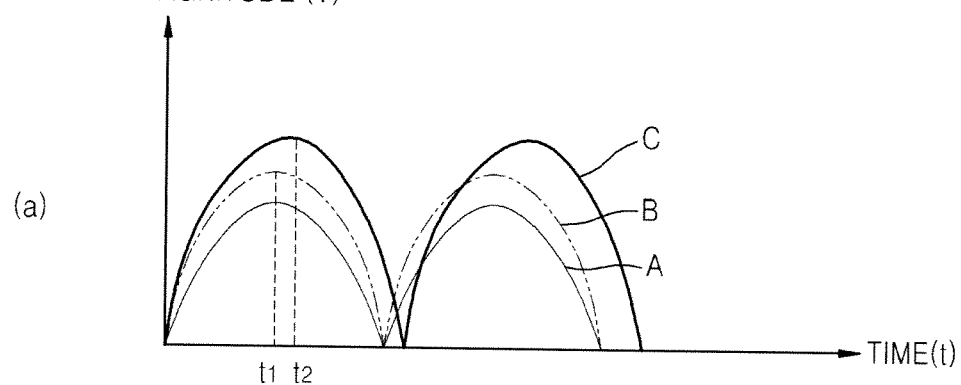
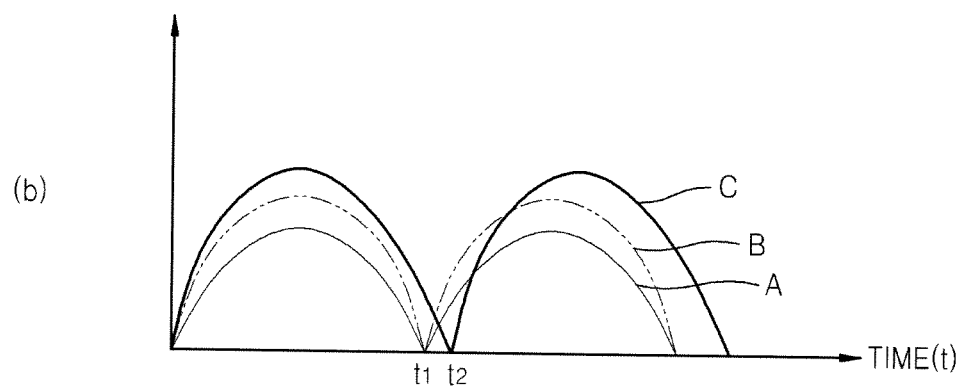

APPARATUS AND METHOD FOR REALIZING SYNCHRONIZATION IMAGE

CROSS-REFERENCE TO RELATED PATENT APPLICATION

This application claims the benefit of Korean Patent Application No. 10-2012-0002033, filed on Jan. 6, 2012, in the Korean Intellectual Property Office, the disclosure of which is incorporated herein in its entirety by reference.

BACKGROUND OF THE INVENTION

1. Field of the Invention

The present invention relates to an apparatus and method for realizing a synchronization image indicating whether motions of an object have been synchronized.

2. Description of the Related Art

Ultrasonic devices are essential equipment for observing an internal structure of an organism. An ultrasonic device, which is a non-invasive inspection device, shows structural details, internal tissues, and flow of fluids in the body.

The ultrasonic device transmits an ultrasonic signal to an object through a body, receives an echo signal reflected from the object, and renders an internal structure of the body into an image.

Inside the body, an object which periodically moves, such as the heart, exists and motions of tissues of the object have to be synchronized with each other. To determine whether the motions of the tissues of the object have been synchronized, a synchronization image produced by the ultrasonic device is mainly used.

A synchronization image is an image regarding motions of an object, and by observing the synchronization image, a tissue which has not been synchronized with other tissues of the object may be discovered.

SUMMARY OF THE INVENTION

The present invention provides a method and apparatus for realizing a synchronization image, in which vector components of tissues of an object are obtained to obtain a velocity magnitude and a velocity direction of each of the tissues.

The present invention also provides a method and apparatus for realizing a synchronization image, in which horizontal-direction velocity magnitudes of tissues of an object are accurately measured to improve the accuracy of a synchronization image of the object.

According to an aspect of the present invention, there is provided a method of realizing a synchronization image, the method including transmitting an ultrasonic signal to an object, obtaining vector components of at least two points included in the object based on an echo signal reflected from the object, and realizing a synchronization image of the object, which indicates whether motions of the at least two points have been synchronized, by using the obtained vector component.

The synchronization image may be a two-dimensional (2D) image or a three-dimensional (3D) image.

The vector components of the at least two points may include velocity magnitudes and velocity directions of the at least two points.

The realizing the synchronization image may include realizing the synchronization image by using time differences among time points at which each of the velocity magnitudes of the at least two points reach a predetermined rate of each of corresponding peak velocity magnitudes of at least two points.

The method may further include obtaining displacements of the at least two points by using the obtained vector components, in which the realizing the synchronization image includes realizing the synchronization image by using time differences among time points at which each of the displacements of the at least two points reach a predetermined rate of each of corresponding peak displacements of the at least two points.

The method may further include setting an arbitrary position in the object and obtaining velocity magnitudes in a direction toward the set position from the velocity magnitudes of the at least two points by using the obtained vector components, in which the realizing the synchronization image includes realizing the synchronization image by using time differences among time points at which each of the velocity magnitudes of the at least two points in the direction toward the set position reach a predetermined rate of each of corresponding peak velocity magnitudes of the at least two points in the direction toward the set position.

The method may further include displaying the realized synchronization image.

The realizing the synchronization image may include realizing the synchronization image by expressing the time differences among time points in a color scale.

According to another aspect of the present invention, there is provided an apparatus for realizing a synchronization image, the apparatus including a transducer for transmitting an ultrasonic signal to an object; a vector component obtaining unit for obtaining vector components of at least two points included in the object based on an echo signal reflected from the object; and an image realizing unit for realizing a synchronization image of the object, which indicates whether motions of the at least two points have been synchronized, by using the obtained vector component.

The synchronization image may be a two-dimensional (2D) image or a three-dimensional (3D) image.

The vector components of the at least two points may include velocity magnitudes and velocity directions of the at least two points.

The image realizing unit may realize the synchronization image by using time differences among time points at which each of the velocity magnitudes of the at least two points reach a predetermined rate of each of corresponding peak velocity magnitudes of the at least two points.

The vector component obtaining unit may obtain displacements of the at least two points by using the obtained vector components, and the image realizing unit may realize the synchronization image by using time differences among time points at which each of the displacements of the at least two points reach a predetermined rate of each of corresponding peak displacements of the at least two points.

The vector component obtaining unit may set an arbitrary position in the object and obtains velocity magnitudes in a direction toward the set position from the velocity magnitudes of the at least two points by using the obtained vector components, and the image realizing unit may realize the synchronization image by using time differences among time points at which each of the velocity magnitudes of the at least two points in the direction toward the set position reach a predetermined rate of each of corresponding peak velocity magnitudes of the at least two points in the direction toward the set position.

The apparatus may further include a display unit for displaying the realized synchronization image.

The image realizing unit may realize the synchronization image by expressing the time differences among time points in a color scale.

The transducer may comprise a 2D matrix probe.

According to another aspect of the present invention, there is provided a computer-readable recording medium having recorded thereon a computer program for executing the method of realizing a synchronization image.

According to another aspect of the present invention, there is provided an ultrasonic device including the apparatus for realizing a synchronization image.

BRIEF DESCRIPTION OF THE DRAWINGS

The above and other features and advantages of the present invention will become more apparent by describing in detail exemplary embodiments thereof with reference to the attached drawings in which:

FIGS. 6A and 6B are graphs for describing examples of a method of realizing a synchronization image by an apparatus for realizing a synchronization image, according to an embodiment of the present invention or another embodiment of the present invention;

DETAILED DESCRIPTION OF THE INVENTION

Figure 1:
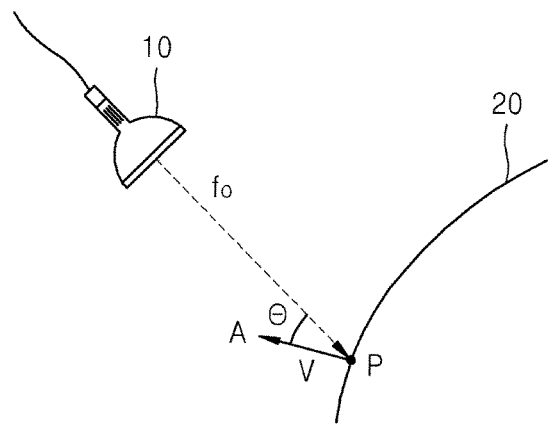
FIG. 1 is a diagram for describing a conventional method of realizing a synchronization image.

Advantages and features of the present invention and a method for achieving them will become apparent from embodiments described below in detail with reference to the accompanying drawings. However, the present invention is not limited to the disclosed embodiments and may be implemented in different forms. The embodiments are provided to complete the disclosure of the present invention and to allow those of ordinary skill in the art to fully understand the scope of the present invention, and the present invention is defined merely by the claims. Throughout the specification, like reference numerals refer to like components.

Terms 'part' used in the embodiments means a software or a hardware component such as a field-programmable gate array (FPGA) or an application-specific integrated circuit (ASIC), and a 'part' plays a certain role. However, the 'part' does not have a meaning limited to software or hardware. The 'part' may be configured to be in a storage medium capable of addressing, or may be configured to execute one or more processors. Therefore, as an example, the 'part' includes components such as software components, object-oriented software components, class components, and task components, and processes, functions, attributes, procedures, subroutines, segments of a program code, drivers, firmware, a micro code, a circuit, data, a database, data structures, tables, arrays, and variables. Functions provided in components and 'parts' may be combined into a smaller number of components and 'parts' or may be further separated into additional components and 'parts'.

FIG. 1 is a diagram for describing a conventional method of realizing a synchronization image.

A general ultrasonic device realizes a synchronization image of an object 20 by using the Doppler effect.

The object 20 means an organ in a body or a particular region in the body for which an ultrasonic image is to be obtained. In addition, in the specification, a 'tissue' means a cell or a group of cells which forms the object 20.

A tissue P of the object 20 moves in a direction A with a velocity magnitude v. A transducer 10 of the general ultrasonic device, once transmitting an ultrasonic signal having a frequency $f_0$ to the tissue P, then receives an echo signal reflected from the tissue P. The frequency of the echo signal changes according to the velocity magnitude v of the tissue P and an angle θ between an output direction of the ultrasonic signal and a movement direction of the tissue P; a difference between a frequency of the ultrasonic signal transmitted to the tissue P and a frequency of the echo signal is referred to as a Doppler frequency. A signal having the Doppler frequency is called a Doppler signal.

The general ultrasonic device obtains a velocity magnitude of each tissue by measuring a Doppler frequency received from each tissue of the object 20, and realizes a synchronization image of the object 20 based on whether time points at which velocity magnitudes of respective tissues reach peak velocity magnitudes of respective tissues coincide with each other.

However, since respective tissues of the object 20 have different velocity directions, the general ultrasonic device cannot accurately measure an angle between the movement direction of each tissue and the transmitted ultrasonic signal. As a result, if an angle between the movement direction of each tissue and the ultrasonic signal transmitted to the tissue is 0 degrees, the general ultrasonic device may accurately measure the velocity magnitude of the tissue, but may not accurately measure the lateral-direction velocity magnitude of the tissue moving in another direction, making it impossible to realize an accurate synchronization image.

Herein, the 'velocity magnitude' is a scalar quantity that indicates only the magnitude of a velocity and not a direction. The 'velocity direction' means a direction in which a particular object or a particular point of an object desires to move at an arbitrary time point.

Figure 2:
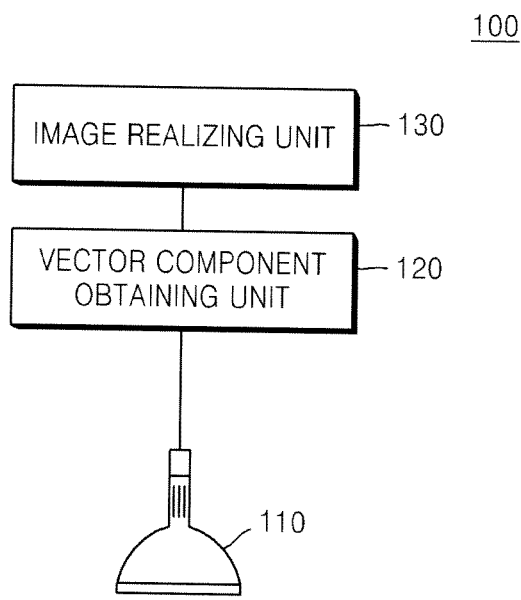
FIG. 2 is a diagram showing a structure of an apparatus for realizing a synchronization image, according to an embodiment of the present invention.

FIG. 2 is a diagram showing a structure of an apparatus 100 for realizing a synchronization image, according to an embodiment of the present invention.

The apparatus 100 for realizing a synchronization image may be included in an ultrasonic device or may be implemented as a microchip.

Referring to FIG. 2, the apparatus 100 may include a transducer 110, a vector component obtaining unit 120, and an image realizing unit 130.

The transducer 110 transmits an ultrasonic signal to an object. The transducer 110 may also receive an echo signal reflected from the object. The transducer 110 may comprises a 2D matrix probe.

The transducer 110 includes a plurality of elements including piezoelectric devices, and each element transmits an ultrasonic signal.

The object may include at least two points. The at least two points according to an embodiment of the present invention may be different tissues in the object or may be different points in the same tissue. In the following description, for convenience's sake, an example in which the at least two points are different tissues in the object is described.

The transducer 110 transmits an ultrasonic signal to each of the tissues of the object, and receives a reflected echo signal. The transducer 110 may transmit the ultrasonic signal to different points in the object and receive the reflected echo signal.

The vector component obtaining unit 120 obtains a vector component of a tissue based on the echo signal reflected from the tissue of the object. The vector component of the tissue may include a velocity magnitude and a velocity direction of the tissue. The vector component obtaining unit 120 may obtain the velocity magnitude and the velocity direction of the tissue based on a Doppler frequency included in the echo signal.

How the vector component obtaining unit 120 obtains the vector component is described in detail below with reference to FIGS. 4 and 5.

The image realizing unit 130 realizes a synchronization image of the object, which indicates whether motions of the tissues of the object have been synchronized, by using the vector component obtained by the vector component obtaining unit 120. The image realizing unit 130 may realize the synchronization image as a 2D image or a 3D image.

Now the image realizing unit 130 realizes the synchronization image is described in detail below with reference to FIG. 6.

Figure 3:
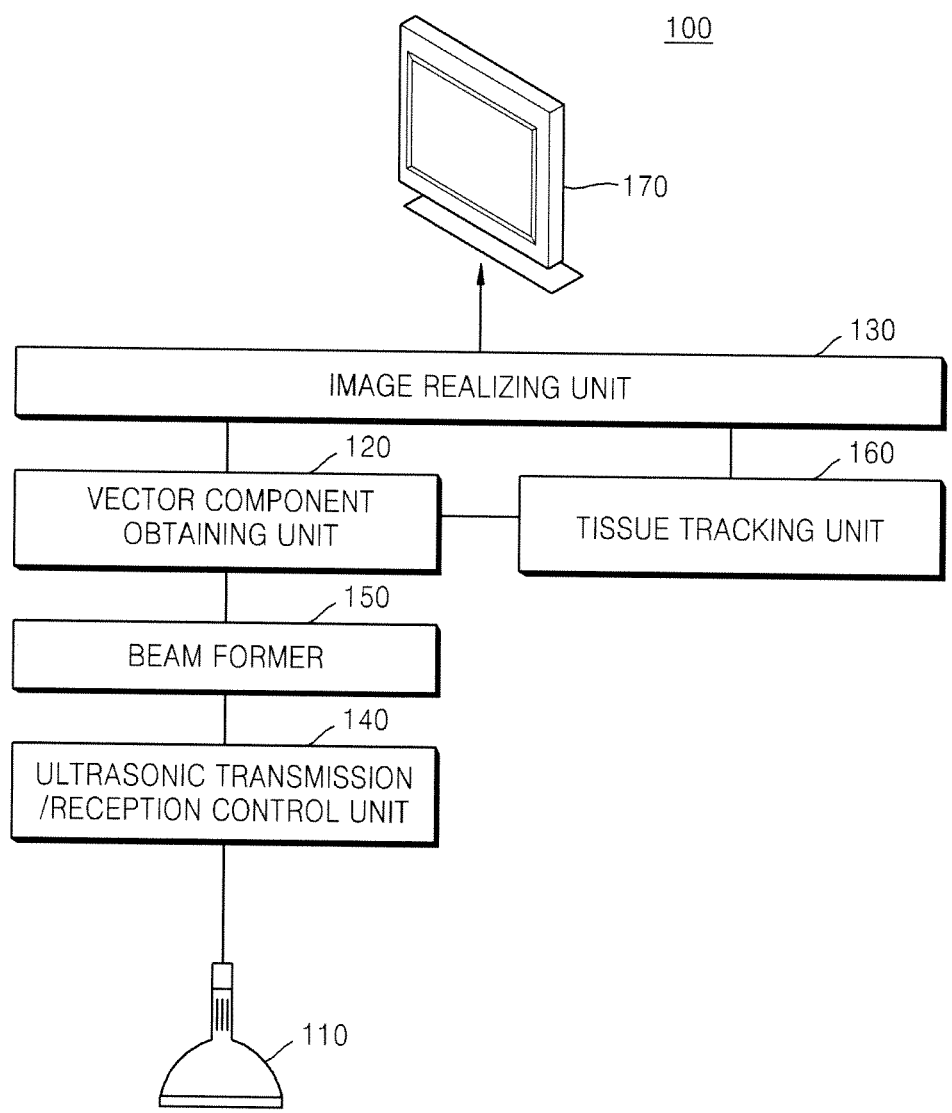
FIG. 3 is a diagram showing a structure of an apparatus for realizing a synchronization image, according to another embodiment of the present invention; to FIG. 4 is a diagram for describing how to obtain a vector component of a tissue of an object by an apparatus for realizing a synchronization image, according to an embodiment of the present invention.

FIG. 3 is a diagram showing a structure of the apparatus 100 for realizing a synchronization image, according to another embodiment of the present invention.

Referring to FIG. 3, the apparatus 100 further includes an ultrasonic transmission/reception control unit 140, a beam former 150, a tissue tracking unit 160, and a display unit 170 in addition to the transducer 110, the vector component obtaining unit 120, and the image realizing unit 130 shown in FIG. 2.

The transducer 110, the vector component obtaining unit 120, and the image realizing unit 130 shown in FIG. 3 have the same technical spirit as those shown in FIG. 2, and thus will not be described in detail.

The ultrasonic transmission/reception control unit 140 controls the transducer 110 to transmit an ultrasonic signal to an object and to receive an echo signal from the object.

Echo signals received through the transducer 110 are sent to the beam former 150, which collects a plurality of received echo signals and converts them into a signal. A distance between each of a plurality of elements included in the transducer 110 and a target tissue varies from element to element, such that the plurality of echo signals reflected from the tissue are not received at the same time point. Therefore, the beam former 150 applies a time delay to the plurality of received echo signals to convert them into a single signal.

The tissue tracking unit 160 tracks the velocity magnitude and the velocity direction of each tissue of the object based on the vector component obtained by the vector component obtaining unit 120.

The display unit 170 displays the synchronization image realized by the image realizing unit 130 to enable a user to identify the synchronization image.

Figure 4:
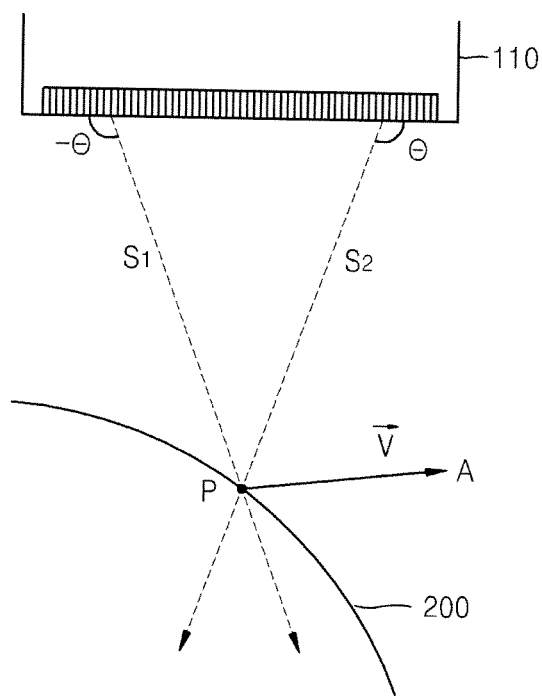

FIG. 4 is a diagram for describing how to obtain a vector component of a tissue of an object 200 by the apparatus 100 for realizing a synchronization image, according to an embodiment of the present invention.

The transducer 110 transmits a first ultrasonic signal $S_1$ and a second ultrasonic signal $S_2$ to a tissue P of the object 200. The tissue P moves in a direction A with a velocity vector $\vec{v}$. The frequencies of the ultrasonic signals $S_1$ and $S_2$ are changed due to the tissue P moving in the direction A, and frequency-changed echo signals may be received by the transducer 110.

Figure 5:
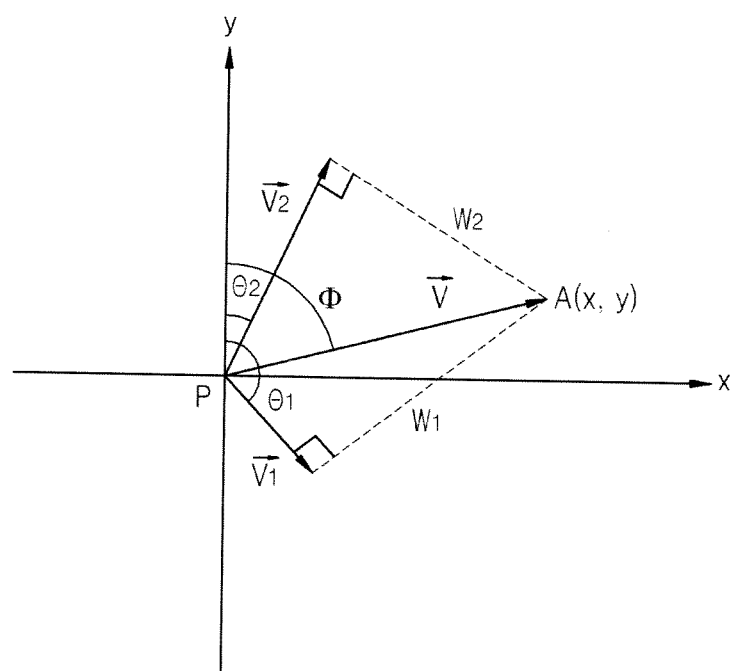
FIG. 5 is a diagram for describing how to obtain a vector component of a tissue of an object by an apparatus for realizing a synchronization image, according to another embodiment of the present invention.

FIG. 5 is a diagram for describing how to obtain a vector component of a tissue of the object 200 by the apparatus 100 for realizing a synchronization image, according to another embodiment of the present invention.

Once the velocity vector $\vec{v}$ of the tissue P is projected in a vertical direction, a velocity vector $\vec{v}_1$ and a velocity vector $\vec{v}_2$ may be obtained. The ultrasonic signal $S_1$ is reflected by the tissue P and transmitted to the transducer 110, and in this case, a generated Doppler signal corresponds to the velocity vector $\vec{v}_1$. The ultrasonic signal $S_2$ is reflected by the tissue P and transmitted to the transducer 110, and in this case, a generated Doppler signal corresponds to the velocity vector $\vec{v}_2$.

By letting an angle difference between an y axis and the velocity vector $\vec{v}_1$ be $\theta_1$ and an angle difference between the y axis and the velocity vector $\vec{v}_2$ be $\theta_2$, the following equations are derived with respect to the velocity vectors $\vec{v}_1$ and $\vec{v}_2$.

$$y = \tan\theta_1 \cdot x \text{ for } \vec{v}_1 \qquad (1)$$

$$y = \tan\theta_2 \cdot x \text{ for } \vec{v}_2 \qquad (2)$$

By letting velocity magnitudes of the velocity vectors $\vec{v}_1$ and $\vec{v}_2$ be $v_1$ and $v_2$, respectively, one-dimensional (1D) straight lines $w_1$ and $w_2$, which are perpendicular to the velocity vectors $\vec{v}_1$ and $\vec{v}_2$, respectively, may be derived as below.

$$y = -(1/\tan\theta_1)x + v_1/\cos\theta_1 \text{ for } w_1 \qquad (3)$$

$$y = -(1/\tan\theta_2)x + v_2/\cos\theta_2 \text{ for } w_2 \qquad (4)$$

The velocity magnitudes $v_1$ and $v_2$ have the following relationship with the Doppler frequencies of the ultrasonic signals $S_1$ and $S_2$:

$$v_n = (\Delta f_n/f) \cdot c \qquad (5),$$

wherein $\Delta f_n$ indicates a Doppler frequency, f indicates the frequencies of the ultrasonic signals $S_1$ and $S_2$, c indicates the sound speeds of the ultrasonic signals $S_1$ and $S_2$, and n is an integer.

Since the ultrasonic signals $S_1$ and $S_2$ are transmitted to a tissue in opposite directions, but with the same angle, $\theta_1$ and $\theta_2$ have the following relationship.

$$\theta_1 = \pi - \theta_2 \qquad (6)$$

$$\cos\theta_1 = -\cos\theta_2 \qquad (7)$$

$$\tan\theta_1 = -\tan\theta_2 \qquad (8)$$

By using Equations 6, 7, and 8, an intersection of Equations 3 and 4 is calculated, from which the following equations are derived.

$$x = \frac{v_1 + v_2}{2} \frac{\sin\theta_2}{\cos^2\theta_2} \quad (9)$$

$$y = \frac{v_2 - v_1}{2\cos\theta_2} \quad (10)$$

x and y of Equations 9 and 10 are coordinates of A.

By using Equations 9 and 10, the velocity magnitude v and an angle Φ with the y axis of the velocity vector $\vec{v}$ are derived as follows:

$$v = |\vec{v}| = \sqrt{x^2 + y^2}$$

$$\phi = \tan^{-1}\frac{y}{x}$$

From the calculated velocity magnitude and angle Φ of the velocity vector $\vec{v}$, the vector component including the velocity magnitude and the velocity direction of the tissue P are obtained.

FIGS. 6A and 6B are graphs for describing examples of a method of realizing a synchronization image by the apparatus 100 for realizing a synchronization image, according to an embodiment of the present invention or another embodiment of the present invention.

FIG. 6A is a graph showing velocity magnitudes v of tissues A, B, and C of an object with respect to time.

Time $t_1$ indicates a time point at which the tissues A and B reach peak velocity magnitudes, and $t_2$ indicates a time point at which the tissue C reaches a peak velocity magnitude.

The image realizing unit 130 may realize a synchronization image by using a velocity magnitude of each tissue. That is, the image realizing unit 130 may realize the synchronization image by using time differences among time points at which the velocity magnitudes of respective tissues reach a predetermined rate of their peak velocity magnitudes.

For example, if the predetermined rate is set to 100% for an object for which synchronization has been completed, then time points at which respective tissues reach their peak velocity magnitudes have to coincide with each other. If the predetermined rate is set to 0% for an object for which synchronization has been completed, then time points at which velocity magnitudes of respective tissues reach 0 have to coincide with each other. A time point at which the velocity magnitude of each tissue reaches 0 means a time point prior to contraction of the object after expansion of the object or a time point prior to expansion of the object after contraction of the object.

Referring to FIG. 6A, it can be seen that time points at which the tissues A and B reach their peak velocity magnitudes coincide with each other, but a time point at which the tissue C reaches its peak velocity magnitude is different from those at which the tissues A and B reach their peak velocity magnitudes. Hence, it can be known that in the object, the tissue C has not been synchronized.

FIG. 6B is a graph showing displacements d of the tissues A, B, and C of the object with respect to time.

The 'displacement' means the amount of change in position, and is defined as a vector quantity having a magnitude and a direction.

Time $t_1$ indicates a time point at which displacements of the tissues A and B become 0, and $t_2$ indicates a time point at which a displacement of the tissue C becomes 0.

The vector component obtaining unit 120 obtains a displacement of each tissue by using the obtained vector component, and the image realizing unit 130 may realize the synchronization image by using the displacement of each tissue. That is, the image realizing unit 130 may realize the synchronization image by using time differences among time points at which displacements of respective tissues reach a predetermined rate of their peak displacements.

For example, if time points at which displacements of respective tissues become 0 coincide with each other for a predetermined rate of 0%, the respective tissues of the object may be regarded as having been synchronized with each other.

Referring to FIG. 6B, time points at which displacements of the tissues A and B reach 0 coincide with each other, but a time point at which the displacement of the tissue C reaches 0 is different from those at which displacements of the tissues A and B reach 0. Therefore, it can be determined that the in the object, the tissue C has not been synchronized.

Figure 7:
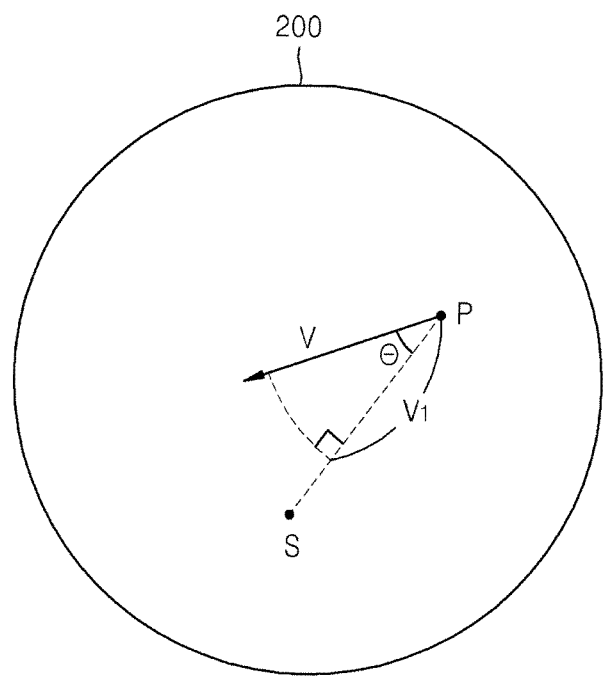
FIG. 7 is a diagram for describing an example of a method of realizing a synchronization image by an apparatus for realizing a synchronization image, according to an embodiment of the present invention or another embodiment of the present invention.

FIG. 7 is a diagram for describing an example of a method of realizing a synchronization image by the apparatus 100 for realizing a synchronization image, according to an embodiment of the present invention or another embodiment of the present invention.

According to another embodiment of the present invention, the vector component obtaining unit 120 may set an arbitrary position S in the object and obtain a velocity magnitude v' in a direction toward the set position S from a velocity magnitude of each tissue of the object, and the image realizing unit 130 may realize a synchronization image by using the velocity magnitude v' of each tissue in the direction toward the set position S.

More specifically, a user or an ultrasonic device may set the arbitrary position S in the object, and the vector component obtaining unit 120 may obtain the velocity magnitude v' in the direction toward the set position S from the velocity magnitude v of the tissue P. The velocity magnitude v' of the tissue P in the direction toward the set position S may be obtained by using an angle difference θ between the tissue P and the set position S and the velocity magnitude v of the tissue P (v'=v·cos θ).

The image realizing unit 130 may realize the synchronization image by using time differences among time points at which velocity magnitudes of respective tissues of the object in the direction toward the set position reach a predetermined rate of their peak velocity magnitudes in the direction toward the set position. In this way, the synchronization image may be realized based on the position desired by the user or the ultrasonic device.

Figure 8:
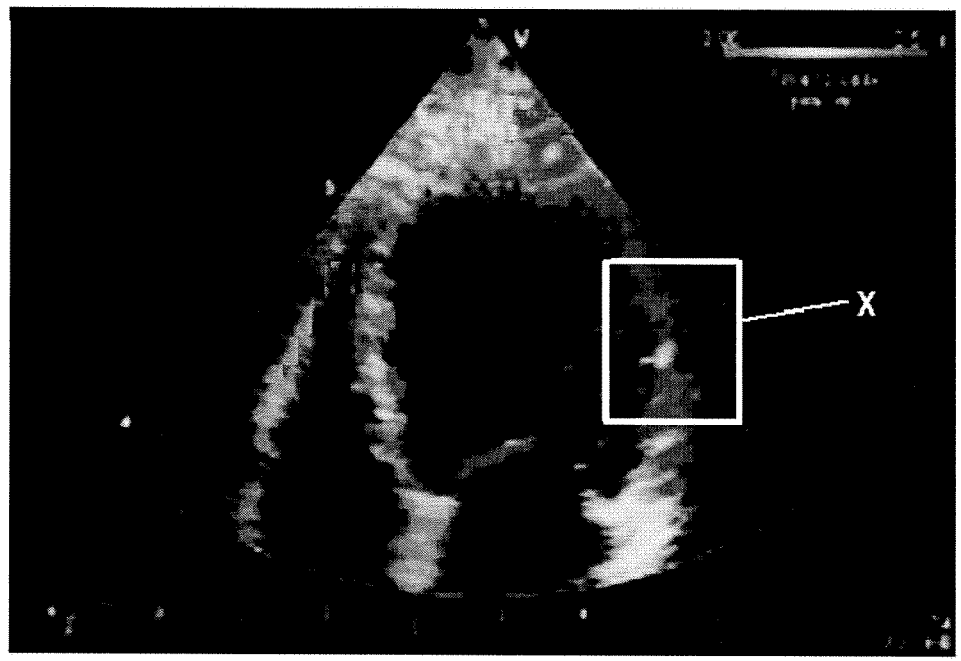
FIG. 8 is a synchronization image of the heart.

FIG. 8 is a synchronization image of the heart.

The image realizing unit 130 of the apparatus 100 according to another embodiment of the present invention may realize a synchronization image by expressing time differences among time points described with reference to FIGS. 6A and 6B in a color scale. That is, a difference between time points at which velocity magnitudes of respective tissues reach a predetermined rate of their peak velocity magnitudes, a difference between time points at which displacements of respective tissues reach a predetermined rate of their peak displacements, and so forth are expressed in a color scale. A portion indicated by 'X' is a synchronization image for the tissue C of FIGS. 6A and 6B.

Figure 9:
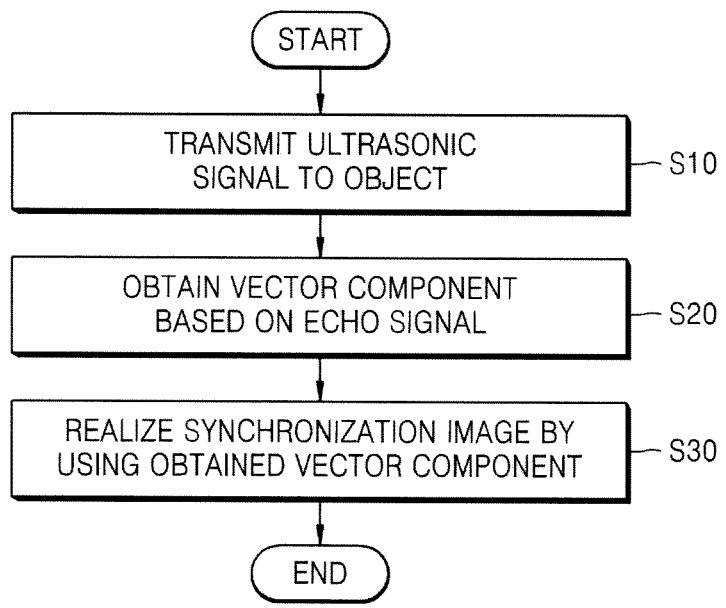
FIG. 9 is a flowchart of a method of realizing a synchronization image, according to an embodiment of the present invention.

FIG. 9 is a flowchart of a method of realizing a synchronization image, according to an embodiment of the present invention. Referring to FIG. 9, the method includes operations that are time-serially processed by the apparatus 100 shown in FIGS. 2 and 3. Therefore, although omitted, the above description of the apparatus 100 shown in FIGS. 2 and 3 also applies to the method shown in FIG. 9.

In operation S10, the transducer 110 transmits an ultrasonic signal to an object including at least two tissues. In addition, the transducer 110 may receive an echo signal reflected from the object. The transducer 110 may transmit an ultrasonic signal to at least two different tissues in the object.

In operation S20, the vector component obtaining unit 120 obtains a vector component of each tissue of the object based on the received echo signal. The vector component of each tissue may include velocity magnitude and velocity direction of each tissue.

In operation S30, the image realizing unit 130 realizes a synchronization image by using the vector component of each tissue of the object. The synchronization image may be realized in a color scale.

The above-described embodiments of the present invention can be implemented as a program which can be executed by a computer, and may be implemented on a general-purpose digital computer which runs the program by using a computer-readable recording medium.

The computer-readable recording medium may include a magnetic storage medium (e.g., ROMs, floppy disks, hard disks, etc.), optical reading medium (e.g., CD-ROMs, DVDs, etc.), etc.

The method and apparatus for realizing a synchronization image, according to embodiments of the present invention, obtain vector components of tissues of the object, thereby obtaining velocity magnitude and velocity direction of motions of the respective tissues.

Moreover, the method and apparatus for realizing a synchronization image, according to embodiments of the present invention, accurately measure horizontal-direction velocity magnitudes of tissues of the object, thereby improving the accuracy of a synchronization image of the object.

While the present invention has been particularly shown and described with reference to exemplary embodiments thereof, it will be understood by those of ordinary skill in the art that the present invention may also be cared out in other concrete forms without changing the technical spirit or essential features of the present invention. Therefore, the above-described embodiments have to be construed as illustrative rather than restrictive.

What is claimed is:

1. A method of realizing a synchronization image, the method comprising:
   transmitting an ultrasonic signal to tissues included in an object expanding and contracting periodically;
   obtaining displacements of at least two points included in the object based on an echo signal reflected from the tissues; and
   realizing a synchronization image of the tissues, which indicates using a color scale whether motions of the at least two points are synchronized, by using time differences among time points at which each of the displacements of the at least two points reach a predetermined rate of each of corresponding peak displacements of the at least two points,
   wherein when motions of the at least two points are not synchronized, the at least two points are represented by different colors in the synchronization image.

2. The method of claim 1, wherein the synchronization image is a two-dimensional (2D) image or a three-dimensional (3D) image.

3. The method of claim 1, further comprising:
   obtaining vector components of the at least two points included in the object based on the echo signal reflected from the tissues,
   wherein the vector components of the at least two points comprise velocity magnitudes and velocity directions of the at least two points.

4. The method of claim 3, wherein the realizing the synchronization image comprises realizing the synchronization image by using time differences among time points at which each of the velocity magnitudes of the at least two points reach a predetermined rate of each of corresponding peak velocity magnitudes of the at least two points.

5. The method of claim 1,
   wherein the displacements of the at least two points included in the object are obtained based on a Doppler frequency included in the echo signal reflected from the tissues.

6. The method of claim 3, further comprising:
   setting an arbitrary position in the object; and
   obtaining velocity magnitudes in a direction toward the set position from the velocity magnitudes of the at least two points by using the obtained vector components,
   wherein the realizing the synchronization image comprises realizing the synchronization image by using time differences among time points at which each of the velocity magnitudes of the at least two points in the direction toward the set position reach a predetermined rate of each of corresponding peak velocity magnitudes of the at least two points in the direction toward the set position.

7. The method of claim 1, further comprising displaying the realized synchronization image.

8. The method of claim 4, wherein the realizing the synchronization image comprises realizing the synchronization image by expressing the time differences among time points in the color scale.

9. An apparatus for realizing a synchronization image, the apparatus comprising:
   a transducer for transmitting an ultrasonic signal to tissues included in an object expanding and contracting periodically;
   one or more processors configured to:
   obtain displacements of at least two points included in the object based on an echo signal reflected from the tissues; and
   realize a synchronization image of the tissues, which indicates using a color scale whether motions of the at least two points are synchronized, by using time differences among time points at which each of the displacements of the at least two points reach a predetermined rate of each of corresponding peak displacements of the at least two points,
   wherein when motions of the at least two points are not synchronized, the at least two points are represented by different colors in the synchronization image.

10. The apparatus of claim 9, wherein the synchronization image is a two-dimensional (2D) image or a three-dimensional (3D) image.

11. The apparatus of claim 9, wherein the one or more processors are further configured to obtain vector components of the at least two points included in the object based on the echo signal reflected from the tissues, and the vector components of the at least two points comprise velocity magnitudes and velocity directions of the at least two points.

12. The apparatus of claim 11, wherein the one or more processors are configured to realize the synchronization image by using time differences among time points at which each of the velocity magnitudes of the at least two points reach a predetermined rate of each of corresponding peak velocity magnitudes of the at least two points.

13. The apparatus of claim 9, wherein the displacements of the at least two points included in the object are obtained based on a Doppler frequency included in the echo signal reflected from the tissues.

14. The apparatus of claim 11, wherein the one or more processors are further configured to:
set an arbitrary position in the object; and
obtain velocity magnitudes in a direction toward the set position from the velocity magnitudes of the at least two points by using the obtained vector components, and
wherein the one or more processors are configured to realize the synchronization image by using time differences among time points at which each of the velocity magnitudes of the at least two points in the direction toward the set position reach a predetermined rate of each of corresponding peak velocity magnitudes of the at least two points in the direction toward the set position.

15. The apparatus of claim 9, further comprising a display for displaying the realized synchronization image.

16. The apparatus of claim 12, wherein the one or more processors are configured to realize the synchronization image by expressing the time differences among time points in the color scale.

17. The apparatus of claim 9, wherein the transducer comprises a 2D matrix probe.

18. A non-transitory computer-readable recording medium having recorded thereon a computer program for executing a method of realizing a synchronization image according to claim 1.

19. An ultrasonic device comprising an apparatus for realizing a synchronization image according to claim 9.

* * * * *